United States Patent [19]

Speaker et al.

[11] Patent Number: 5,093,198
[45] Date of Patent: Mar. 3, 1992

[54] ADJUVANT-ENHANCED SUSTAINED RELEASE COMPOSITION AND METHOD FOR MAKING

[75] Inventors: Tully J. Speaker; Tycho J. Speaker, both of Philadelphia, Pa.; John H. Collett, Sale, England

[73] Assignee: Temple University, Philadelphia, Pa.

[21] Appl. No.: 417,590

[22] Filed: Oct. 5, 1989

Related U.S. Application Data

[63] Continuation-in-part of Ser. No. 64,820, Jun. 19, 1987, abandoned.

[51] Int. Cl.$^5$ ............................ A61K 9/58; A61K 9/60; B01J 13/10
[52] U.S. Cl. ............................ 428/402.21; 427/213.3; 424/461; 424/493; 428/402.24; 514/963
[58] Field of Search ............... 427/213.3; 428/402.21, 428/402.24; 424/461, 493; 514/963

[56] References Cited

U.S. PATENT DOCUMENTS

| | | | |
|---|---|---|---|
| 3,096,248 | 7/1963 | Rudzki | 264/112 |
| 3,231,619 | 1/1966 | Speranza | 564/505 |
| 3,565,559 | 2/1971 | Sato et al. | 264/43 X |
| 3,575,882 | 4/1971 | Vandegaer et al. | 428/402.2 X |
| 3,872,171 | 3/1975 | Cronin et al. | 564/506 |
| 3,909,441 | 9/1975 | Ohyama et al. | 428/402.2 X |
| 3,959,457 | 5/1976 | Speaker et al. | 428/402.2 X |
| 3,959,460 | 5/1976 | Vanlergerghe et al. | 424/70 |
| 3,983,171 | 9/1976 | Vanlerberghe et al. | 562/581 |
| 4,003,846 | 1/1977 | Kuhn et al. | 428/402.2 X |
| 4,166,132 | 8/1979 | Kraska | 514/668 |
| 4,324,683 | 4/1982 | Lim et al. | 428/402.2 X |
| 4,330,677 | 5/1982 | Linke et al. | 562/582 |
| 4,461,759 | 7/1984 | Dunn | 424/465 |

FOREIGN PATENT DOCUMENTS 0299205  11/1989  European Pat. Off. .

*Primary Examiner*—Richard D. Lovering
*Attorney, Agent, or Firm*—Ratner & Prestia

[57] ABSTRACT

Improved sustained-release delivery forms comprising Lewis acid-Lewis base salt microparticulate material modified by the addition of at least one additional constituent known as an "adjuvant" selected from the group consisting of carbomers, poloxamers and tetronomers. Adjuvants may assist in the manufacture of the microparticle or may provide additional advantageous characteristics such as assisting in solubilizing a core material or forming of the microparticle wall or both. Adjuvant modified microparticles have improved controlled release characteristics, have greater mechanical and thermal stability and have increased capacity for a wide range of core materials. In general, adjuvants are polyether linkage-containing molecules, adapted by virtue of their otherwise strongly acidic (carbomers or other water soluble compounds with pKa of less than 5), strongly basic (tetronomers or other non-aqueous solvent soluble bases with a pKa of more than 9 or above) or essentially neutral, but extremely weakly basic characteristics (poloxamers or other non-aqueous solvent soluble compounds with a pKa of from 5 to 7) to function as wall-forming or core-forming reactants in the microcapsule-forming reaction of this invention.

12 Claims, No Drawings

ADJUVANT-ENHANCED SUSTAINED RELEASE COMPOSITION AND METHOD FOR MAKING

BACKGROUND OF THE INVENTION

This application is a continuation-in-part of U.S. patent application Ser. No. 07/064,820, filed June 19, 1987 now abandoned, of common assignment and partial common inventorship herewith.

This invention pertains to novel microparticulate material, the particles of which are sometimes referred to as microcapsules, and to a method for making such material. More specifically, this invention pertains to an improved microparticulate material, formed by the addition of one or more adjuvants, wherein said improved microparticles may act as a carrier for diffusable reactants, such as chemicals and pharmaceuticals, in order to serve as sustained or controlled release "microencapsulated" delivery forms.

Microencapsulation is a technique of enclosing core materials within a polymeric membrane to produce microparticles. The encapsulated material may be released over a period of time by diffusion or immediately by crushing or by digesting the shell-like wall of the microparticle. These types of microparticles are used extensively in the dye industry and in the food and cosmetic industries.

In the pharmaceutical industry, considerable interest has been generated by the use of microparticles as sustained release drug delivery formulations. However, many microparticle formulations are of limited utility because of their relatively large particle size. A particle size of greater than that of an erythrocyte (about 7 microns) is not suitable to be injected intravenously.

Further problems with known prior art microparticulate material arise from the fact that generally such material tends to agglomerate, thus deleteriously affecting certain important properties of the materials such as dispersibility. Additionally, microparticulate material which is of suitable size for injection may be captured by the reticuloendothelial system, which could have deleterious effects on blood clearance of the microparticle shell material and tissue distribution of the encapsulated core material.

A specific type of microparticulate material and a method of making such material is disclosed in U.S. Pat. No. 3,959,457 (of common inventorship and assignment herewith). This material is comprised of the reaction product produced at the inter-phase boundary of a finely dispersed emulsion, comprising:

I) a water immiscible solution of an organic polyfunctional Lewis base in a low boiling point, slightly polar, organic solvent; and II) an aqueous solution of a partially hydrophilic, partially lipophilic, polyfunctional Lewis acid.

Microparticles of this type comprise a multiplicity of closed structures formed of lattice-like high molecular weight salt molecules of the Lewis acid and Lewis base, through which an encapsulated core material diffuses. The rate of diffusion is controlled by both the particle or molecular size of the encapsulated compound and by the openness of the lattice or network of molecules comprising the particle walls. The degree of openness of the lattice is controlled by the spacing of reactive sites on the high molecular weight polyfunctional Lewis acids and by the thickness of the particle walls.

In Lewis acid-Lewis base salt microparticles, of the type referred to above, the degree to which diffusibility can be controlled is somewhat limited. There are also some limitations on the type and number of compounds which these microparticles can encapsulate, or which are soluble and stable in polar organic solvents of the type typically used in making these microparticles.

Information Disclosure Statement

U.S. patents cited in the parent of the present application are:

U.S. Pat. No. 3,096,248*—Rudzki (shows carbomer-type materials as tablet coating (i.e., "encapsulant") by "fusion compression.")

U.S. Pat. No. 3,565,559*—Sato et al. (Pluronic and tetronic polymers as surfactants in an encapsulant made by gel phase inversion.)

U.S. Pat. No. 3,575,882—Vandegaer et al. (cited to show "state of art.")

U.S. Pat. No. 3,909,441—Ohyama et al. (cited to show "state of art.")

U.S. Pat. No. 4,003,846—Kuhn et al. (cited to show "state of art.")

U.S. Pat. No. 4,324,683—Lim et al. (cited to show "state of art.")

U.S. Pat. No. 3,959,457—Speaker et al. (Lewis Acid-Lewis Base in separate phases of dispersed emulsion, with basic reactant and a non-reactive core material in non-aqueous discontinuous phase, react at phase interface to form microcapsules; polyethylene glycol disclosed as a possible basic wall-forming reactant.)

* indicates relied upon in rejection of parent application claims.

The following patents were specifically cited in a preliminary patentability search conducted prior to the filing of the parent of the present application:

U.S. Pat. No. 3,231,619 (formation of alkylene oxide adduct);

U.S. Pat. No. 4,330,677 (formation of surface active ethers);

U.S. Pat. No. 3,983,171 (polyhydroxylated polyether chain compounds with lipophilic and carboxylic substituents as anionic surface active agents);

U.S. Pat. No. 3,959,460 (polyhydroxy chain compounds with lipophilic and carboxylic substituents as anionic surface active agents);

U.S. Pat. No. 4,461,759 (sustained release dosage composition, veropamil, acrylic acid polymer);

U.S. Pat. No. 3,872,171 (polyamino polyethers, antiviral agents); and

U.S. Pat. No. 4,166,132 (polyamino polyethers, antiviral agents).

Additionally, EPO Publication No. 0 299 205 (corresponding application which includes the substance of the Speaker et al. parent application) has been published with an apparent "publication date" of Jan. 18, 1989.

No representation or admission is made as to the completeness of the search which has been made, or as to the relevance of the foregoing to the patentability of the invention disclosed and claimed herein.

BRIEF DESCRIPTION OF THE INVENTION

This invention comprises Lewis acid-Lewis base salt microparticulate materials of the type referred to above which include at least one additional constituent, known as an "adjuvant". The adjuvant may be a carbomer, such as high molecular weight polymers of acrylic acid cross-linked with a polyalkenyl polyether, or a polyoxamer, such as a polyoxyethylene-polyoxypropylene copolymer, or a tetronomer, such as a polyoxyethylene adduct of ethylenediamine. The carbomer is acidic and acts as an acid wall-forming reactant. It therefore must be soluble in the aqueous phase of the reactant emulsion. The tetronomer is basic and acts as a basic wall-forming reactant. It therefore must be soluble in the non-aqueous phase. The poloxamer is essentially neutral and is dispersed or dissolved in the non-aqueous phase so that it is entrapped as part of the core material in the final product. The essentially neutral core-forming adjuvant may exhibit basic properties in the presence of an acid due to the formation of oxonium ions at the etheral linkages. Therefore, the core forming adjuvant is always combined, in the non-aqueous phase, with a much more basic wall-forming reactant, such as piperazine, or the tetronomer adjuvant of the present invention.

The common characteristic of the various adjuvants used in the present invention is that each includes polyether linkages. Apart from these linkages, however, the adjuvants are strongly basic (tetronomers), strongly acidic (carbomers), or slightly basic but essentially neutral (poloxamers). The latter (acidic, basic, or essentially neutral) characteristic determines the ultimate location of the polyether linkages in the final microcapsule product. Whether ultimately in the wall structure (by virtue of inclusion in the acid and/or the basic wall forming reactant), or the core, these linkages are believed to contribute to the more robust, more stable characteristics, and greater tolerance (to different core materials) of microcapsules made in accordance with the present invention. Somewhat different effects are believed to be achievable dependent on the location of these polyether linkage sites in the microcapsules.

It is also important, however, that the adjuvants of this invention each have at least some qualitatively defined acidic or basic activity or lack thereof. To be specific, the adjuvants of this invention are classifiable into three groups. All three groups include polyether linkages. The first group, the acidic wall-forming adjuvant, must be soluble in the aqueous phase of the reactant emulsion and should have a pKa of 5 or less. The second group, the basic wall-forming adjuvant, must be soluble in the slightly polar solvent of the dispersed phased in the reactant emulsion and should have a pKa of at least 9. The third group, extremely weak basic, but essentially neutral, core-forming adjuvant should also be soluble in the slightly polar solvent of the dispersed phase in the reactant emulsion and should have a pKa in the range of 5 to 7. That is, the very weak base, if protonated, must lose its proton (ionized as an acid) when the acidity of the surrounding medium is in a pH range greater than about 5. Further, a strongly basic wall-forming reactant having a pKa of at least 9 must also be included in the non-aqueous phase whenever a polyether linkage-containing weak basic, but essentially neutral, adjuvant is used. By way of example, the pKa's of some of the common reactants discussed and exemplified herein are (approximately):

| | |
|---|---|
| Carbomer | 4.5 |
| Tetronomer | 9 |
| Poloxamer | 5 |
| Piperazine | 9 |
| Arabic acid | 4.5 |
| Acacia | 4.5 |
| Polyacrylic acid | 4.5 |

-continued

| | |
|---|---|
| Ethylene diamine | 10 |

Polyethylene glycol (a polyether-linkage-containing, basic wall-forming reactant disclosed in the above-referenced U.S. Pat. No. 3,957,457—Speaker et al.) has a pKa of about 5. As a wall-forming reactant, polyethylene glycol produces characteristically unstable microcapsules, a disadvantage overcome with the present invention.

As used herein, the term "adjuvant," refers to a class of compounds which provide some advantageous characteristics to the microcapsule. An adjuvant may assist in solubilizing a core material in the non-aqueous solvent or may assist in the formation of the microparticle wall or may assist both of these functions.

Furthermore, the adjuvant may provide additional advantageous characteristics to the microparticle such as further controlling the sustained release of the encapsulated core material, or it may assist in the manufacture of the microparticulate material by accelerating the phase separation of the aqueous and non-aqueous solutions.

In some instances, the adjuvants having acidic or basic functions may be used in place of, rather than in addition to, the Lewis acids or Lewis bases of U.S. Pat. No. 3,959,457.

DETAILED DESCRIPTION OF THE INVENTION

Generally, microparticles of the type to which this invention is directed are made as follows:

A non-aqueous solution of a Lewis base in a slightly polar solvent is added to an aqueous solution of a Lewis acid, such as acacia gum, or arabic acid, or carboxymethylcellulose. The Lewis base may be, for example, piperazine, or triethylenediamine, or ethylenediamine. These solutions are combined with rapid stirring to produce a finely dispersed emulsion of organic phase droplets in a continuous aqueous phase. Included in the non-aqueous solvent is a core material such as a drug. For purposes of sustained release of the core material, it must be of such molecular size that it will be able to diffuse out of the individual microparticulate material.

In the organic phase droplets of the finely dispersed emulsion of the aqueous and non-aqueous solutions, the polyfunctional Lewis base is drawn to the surface of the droplet by the polar attraction of the surrounding aqueous phase. In the aqueous phase, the partially hydrophilic, partially lipophilic, polyfunctional Lewis acid is drawn, due to its partially lipophilic characteristic towards the interface between the organic droplet and the surrounding aqueous phase where it reacts, presumably through dipole and/or ionic bonding, with the polyfunctional Lewis base concentrated on the outer surfaces of the organic phase droplets adjacent the interface, to produce a shell-like insoluble particle generally corresponding in shape and size to the organic droplets. Each of these shell-like particles is thought to consist of an open network, or lattice, of molecules of a dipole and/or ionic salt.

The reaction of the polyfunctional Lewis acid and the polyfunctional Lewis base is thought to be essentially a two-step reaction sequence resulting in the formation of anisotropic salt films in small spherical or sphere-like shapes sometimes referred to as microcapsules. The generalized reaction sequence is more clearly set out in U.S. Pat. No. 3,959,457.

In accordance with the present invention, also included in the emulsion is at least one adjuvant, which may be dissolved in the aqueous solution or in the non-aqueous solvent or both, prior to combining the aqueous and non-aqueous solutions. Selected adjuvants must, of course, be substantially non-reactive with other components in the reaction medium (except, of course, as intended for the microcapsule-forming reactions as disclosed herein) and must also be substantially soluble in the appropriate solvent phase.

Adjuvants are of two types, wall-forming and core-forming. Core-forming adjuvants are understood to be entirely within the core of the finished microcapsule. Core-forming adjuvants are typically polyoxyethylene-polyoxypropylene copolymers or block copolymers thereof. They are referred to herein as "poloxamers" and are added to the non-aqueous, slightly polar organic phase before the emulsification step.

Wall-forming adjuvants contribute to both wall and core formation. They combine in their molecular structures either acidic or basic functions together with polyether chains of varying length. Wall-forming adjuvants which combine acidic functional groups with ether chains are exemplified by high molecular weight polymers of acrylic acid cross-linked with a polyalkenyl polyether; such adjuvants are referred to herein as "carbomers". Wall-forming adjuvants which combine basic functional groups with polyether chains are exemplified by ethylene oxide adducts of ethylenediamine, and are referred to herein as "tetronomers".

Both carbomers and tetronomers react with ionizable species at the inter-phase boundary during the wall-forming process to form salts which become integral components of the ionic salt wall structure of the microcapsule. The polyether chains of carbomers and tetronomers are thought to project inwardly from the inner surface of the microcapsule wall for short distances, into what might otherwise be thought of as a core space.

In practice, carbomers are dissolved in the aqueous phase of the manufacturing system. Tetronomers are dissolved in the non-aqueous, slightly polar organic phase. Tetronomers and carbomers fulfill a primary function as wall-forming materials and also act as adjuvants.

GENERAL PROCEDURES FOR FORMING MICROCAPSULES

In all instances where an aqueous solution is utilized as the continuous phase for the dispersion or emulsification of a second solution of materials dissolved in an organic solvent, it is preferred, but not essential, that the organic solvent be slowly and steadily added to the aqueous solution over a period of approximately 30 seconds. In all instances, solutions are prepared and reactions take place at room temperature, unless otherwise stated. Any of several means to disperse or emulsify the organic solution in the aqueous medium may be employed including:

a. vigorously stirring the solution with a magnetically driven stirring bar at a nominal shear rate, generally 700 or more cm/s;

b. vigorously mixing the solution with a multi-orifice axial turbine (such as a Brinkmann homogenizer PT10/35 and generator PST/10, Brinkmann Instruments, Westbury, N.Y.) at a nominal setting of 5; or c. vigorously agitating the solutions with an ultrasonic probe (such a Heat Systems model W185D, Ultrasonics, Inc., Plainview, N.Y.) at a nominal output of 100 watts.

GENERAL EXAMPLE OF METHOD OF MAKING MICROCAPSULE PRODUCTS CONTAINING CORE-FORMING ADJUVANT MATERIALS

An aqueous solution of arabic acid was prepared by adding to one gram of arabic acid, enough water to make 10 mL. Typically, the arabic acid is first wetted with a small amount of alcohol to assist in solubilizing the otherwise slowly solubilized Lewis acid. A non-aqueous solution was also prepared by adding anhydrous piperazine (in an amount stoichiometrically equivalent to the arabic acid), 1.0 g of a core material (acetanilide), and 1.0 g of poloxamer (polyoxyethylene-polyoxypropylene block copolymer, such as Pluronic F68, a product of BASF-Wyandotte Corp., Wyandotte, Ill.), to enough dichloromethane to make 10 mL of solution.

The aqueous and non-aqueous solutions were then combined in a container and continuously agitated for approximately one minute, to produce an emulsion of organic droplets, approximately 5 microns in diameter, dispersed in and surrounded by continuous phase aqueous solution.

Upon standing after agitation, the non-aqueous organic phase was allowed to separate from the aqueous phase. The essentially-clear, non-aqueous organic phase was then removed from the aqueous phase containing the microcapsules. The milk-like suspension of newly formed microcapsules settled to the bottom of the container. Unreacted or excess reaction components were then removed by adding an equal amount of water to the microcapsules and subsequent removal of the added water. Residual dichloromethane was removed by evaporation upon exposure of the microcapsules to the atmosphere. The suspension of dichloromethane-free microcapsules was centrifuged to produce a flowable concentrate of microparticulate material comprised of microcapsules consisting of shell-like films surrounding the core material (acetanilide) and the adjuvant.

GENERAL EXAMPLE OF METHOD OF MAKING MICROCAPSULE PRODUCTS CONTAINING WALL-FORMING ADJUVANT MATERIALS

Microparticulate material prepared by the process of the present invention can be prepared by omitting either the conventional Lewis acids or the conventional Lewis bases. In these products, polymers of acrylic acid providing an acidic moiety) cross-linked polyalkenyl polyethers (providing an adjuvant moiety) may perform the function of the Lewis acid. The Lewis bases may also be substituted for by the use of polyoxyethylene adducts (the adjuvant moiety) of ethylenediamine (the Lewis base moiety).

In both cases the polyether part of the Lewis acid or Lewis base molecule functions as an adjuvant in accordance with the present invention. For example, an aqueous solution of a carbomer was prepared by adding to 0.1 g of finely divided polyacrylic acid cross-linked with polyalkenyl polyethers (a product of Rohm and Haas Company, Philadelphia, Pa.) enough water to make 10 mL. A non-aqueous solution was also prepared by adding a stoichiometric amount of anhydrous piperazine and 1.0 g of a core material (acetanilide) to enough dichloromethane to make 10 mL.

The aqueous and non-aqueous solutions were then combined in a container and continuously agitated for approximately 1 minute to produce an emulsion of organic droplets of approximately 5 microns in diameter in continuous phase comprising the aqueous solution.

The resulting product was handled as previously described, yielding a flowable microparticle material comprised of microcapsules consisting of shell-like films surrounding the core material.

Alternatively, for example, an aqueous solution of arabic acid was prepared by adding to 1.0 g of arabic acid enough water to make 10 mL. A non-aqueous solution was also prepared by adding 1.0 g of core material (acetanilide) and 1.0 g of a polyoxyethylene adduct of ethylenediamine (such as Tetronic 702, a product of BASF-Wyandotte Corp., Wyandotte, Ill.), to enough dichloromethane to make 10 mL.

The aqueous and non-aqueous solutions were then combined in a container and continuously agitated for a minute to produce an emulsion of organic droplets, approximately 5 microns in diameter, in an aqueous continuous phase. The resulting product was handled as previously described, to yield a flowable microparticulate material consisting of shell-like films surrounding the core material.

Adjuvant-containing microparticles of the present invention are physically more robust and are able to withstand greater mechanical and thermal stress than non-adjuvant containing microparticles. For example, when warmed in a water suspension of approximately 40° C., the non-adjuvant containing microparticles of U.S. Pat. No. 3,959,457 will readily dissolve. Conversely, adjuvant containing microparticles of the present invention, comprised of essentially the same Lewis acid-Lewis base combinations, are stable under these conditions and only begin to dissolve at temperatures near 80° C. Similarly, continued agitation of non-adjuvant containing microparticles can result in their rupture while adjuvant containing microparticles are able to withstand vigorous shaking for extended periods.

Furthermore, adjuvant-modified microparticles may facilitate encapsulation of a wider range and/or greater amount of core materials. Many substances are more readily and more extensively soluble in adjuvant-containing, non-aqueous manufacturing solvents, than in those same solvents without the adjuvant. For example, piperazine arabate walled microcapsules containing mineral oil as a core material may be seen to begin to coalesce within minutes after manufacture and may be seen to degrade extensively and to separate into aqueous and oily layers, free of capsular material, within hours after manufacture. However, the addition of a core-forming adjuvant (such as the polyoxyethylene-polyoxypropylene block copolymer, Pluronic F68) to the organic phase before the emulsification step results in producing piperazine arabate walled microcapsules of mineral oil which remain stable for months. The microencapsulation of mineral oil, through the use of an adjuvant, demonstrates the encapsulation of a wider range of core materials than had been possible without the use of an adjuvant.

Furthermore, the use of a core-forming adjuvant enables greater concentrations of relatively polar core materials, such as acetanilide, to be dissolved in the dichloromethane phase. Thus more core material can be encapsulated than is possible without the adjuvant.

Additionally, acidic drugs, such as certain non-steroidial anti-inflammatory agents, exemplified by salicylic acid and ibuprofen, which interfere with wall formation in non-adjuvant containing microparticles, may successfully be encased in adjuvant containing microparticles.

Release of core materials (e.g., a drug) from the adjuvant-containing microparticles of the present invention can be more extensively controlled than can release from non-adjuvant containing microparticles made according to the teachings of U.S. Pat. No. 3,959,457. For example, in the absence of an adjuvant, a quite water soluble substance, such as the model drug acetanilide, may be released from microcapsules into surrounding aqueous medium essentially completely within the space of an hour. However, the addition of a small amount of a core-forming adjuvant can increase the duration of the period of release by at least a factor of 10. In effect, the core-forming adjuvant modifies the release properties of the microcapsular system so that, while it retains the diffusional barrier provided by the capsular wall, release of the drug from the adjuvant-containing system is influenced by the partitioning equilibrium between the adjuvant and the small volume of water which diffuses into the capsule. Thus, the proportion of adjuvant to active core material (e.g., acetanilide) in the microcapsule formulation and the rate of release of active core material are inversely proportional, all other factors being held constant.

Not only may the ratio of core-forming adjuvant to active core material be modified, but the wide range of compositions of core-forming adjuvants with markedly different partitioning characteristics for the same substance allow a second means of controlling rates of release of the active core component.

Independently, the wall-forming adjuvants, by virtue of the differences in ionic lattice spacing of the microcapsules they provide, afford yet another means of controlling rates of release of active core components. It is these three variables, the ratio of core-forming adjuvant to active core component, the range of partitioning coefficient of the active core component between core-forming adjuvants and water, and the lattice structure variation available from wall-forming adjuvants which provide extensive control of the release rate for encapsulated substances.

Thus, the improved controlled release characteristics of adjuvant-modified microparticles, coupled with the improved capacity of such microparticles, allow formulation of microparticles capable of uniform sustained release of core components over a greatly extended period of time.

While this invention has been described with reference to specific, and particularly, preferred embodiments thereof, it is not limited thereto and the appended claims are intended to be construed to encompass not only the specific forms and variants of the invention shown but to such other forms and variants as may be devised by those skilled in the art without departing from the true spirit and scope of this invention.

We claim:

1. Microparticulate material, consisting essentially of the reaction product of an emulsion of:
   a) a partially hydrophilic, partially lipophilic, polyfunctional Lewis acid in an aqueous solution, said solution comprising a continuous phase; and
   b) a polyfunctional Lewis base dissolved in a slightly polar non-aqueous solvent, and a core material dispersed therein, said non-aqueous solvent comprising a discontinuous droplet phase, said continuous aqueous phase surrounding the droplets of said discontinuous phase, wherein, said Lewis acid and said Lewis base and said non-aqueous solvent are adapted by reaction of said Lewis acid and said Lewis base at the phase interface on the surfaces of said droplets to form enclosed cellular structures comprising a microparticulate material containing said core material in said closed structures, in a manner to permit controlled release of the core material through the microparticle wall, said emulsion further including at least one adjuvant selected from the group consisting of poloxamers, which function as part of said core material, and tetronomers, which function as at least part of said Lewis base, said tetronomers and said poloxamers, if present, being disposed in said non-aqueous phase, said non-aqueous phase also including, if poloxamer is present, a basic wall-forming reactant having a pHa of at least 9.

2. Microparticulate material as set forth in claim 1 wherein the adjuvent is a poloxamer.

3. Microparticulate material as set forth in claim 2 wherein the poloxamer is polyoxyethylene-polyoxypropylene or a block copolymer thereof.

4. Microparticulate material as set forth in claim 1 wherein the adjuvant is a tetronomer.

5. Microparticulate material as set forth in claim 4 wherein the tetronomer is a polyoxyethylene adduct of ethylenediamine.

6. In a method of producing microparticulate material comprising:
  a) making a mixture of an aqueous solution of a partially hydrophilic, partially lipophilic, polyfunctional Lewis acid, with a water immiscible solution of a polyfunctional Lewis base in a slightly polar solvent, said water immiscible solution containing a core material;
  b) agitating said mixture to form an emulsion of water immiscible solution droplets surrounded by a continuous phase of said aqueous solution, wherein said Lewis acid and said Lewis base are adapted to react with one another at the common phase interface of said droplet surfaces to form microparticulate material comprising a multiplicity of closed cellular structures containing said core material;
  c) separating and washing and removing residual solvent from said microparticulate material,
  the improvement consisting of including in said mixture at least one adjuvent selected from the group consisting of poloxamers, which function as part of said core material, and tetronomers, which function as at least part of said Lewis base,
  said tetronomers and said poloxamers, if present, being disposed in said water immiscible phase, said water immiscible phase also including, if poloxamer is present a basic wall-forming reactant having a pKa of at least 9.

7. A method of producing microparticulate material as set forth in claim 6, wherein said adjuvant is a tetronomer and is added to said water immiscible solution prior to forming said mixture.

8. A method of producing microparticulate material as set forth in claim 6, wherein said adjuvant is a poloxamer, which is added to said water immisible solution prior to forming said solution.

9. A method of producing microparticulate material as set forth in claim 6 wherein said adjuvant is polyoxyethylene-polyoxypropylene or block copolymers thereof.

10. A method of producing microparticulate material as set forth in claim 6 wherein said adjuvant is a polyoxyethylene adduct of ethylene-diamine.

11. Microparticulate material, consisting essentially of the reaction product of an emulsion of:
  a) a partially hydrophilic, partially lipophilic, polyfunctional Lewis acid in an aqueous solution, said solution comprising a continuous phase; and
  b) a polyfunctional Lewis base dissolved in a slightly polar non-aqueous solvent, and a core material dispersed therein, said non-aqueous solvent comprising a discontinuous droplet phase, said continuous aqueous phase surrounding the droplets of said discontinuous phase,
  wherein, said Lewis acid and said Lewis base and said non-aqueous solvent are adapted by reaction of said Lewis acid and said Lewis base at the phase interface on the surfaces of said droplets to form enclosed cellular structures comprising a microparticulate material containing said core material in said closed structures, in a manner to permit controlled release of the core material through the microparticle wall,
  said emulsion including at least one adjuvant selected from the group consisting of:
    (i) a polyether linkage-containing basic wall-forming reactant dissolved in said slightly polar non-aqueous solvent and having a pKa of at least 9, and
    (ii) an extremely weak basic, but essentially neutral core-forming reactant, having a pKa of 5–7, disposed n said slightly polar non-aqueous solvent phase, said solvent phase also including, if (ii) is present, a basic wall-forming reactant having a pKa of at least 9.

12. In a method of producing microparticulate material comprising:
  a) making a mixture of an aqueous solution of a partially hydrophilic, partially lipophilic, polyfunctional Lewis acid, with a water immiscible solution of a polyfunctional Lewis base in a slightly polar solvent, said water immiscible solution containing a core material;
  b) agitating said mixture to form an emulsion of water immiscible solution droplets surrounded by a continuous phase of said aqueous solution, wherein said Lewis acid and said Lewis base are adapted to react with one another at the common phase interface of said droplet surfaces to form microparticulate material comprising a multiplicity of closed cellular structures containing said core materials;
  c) separating and washing and removing residual solvent from said microparticulate material,
  the improvement consisting of including in said emulsion at least one adjuvant selected form the group consisting of:
    (i) a polyether linkage-containing basic wall-forming reactant dissolved in said water immiscible solution and having a pKa of at least 9, and
    (ii) an extremely weak basic, but essentially neutral core-forming reactant, having a pKa of 5–7, disposed in said water immiscible solution, said water immiscible solution also including, if (ii) is present, a basic wall-forming reactant having a pKa of at least 9.

* * * * *